United States Patent [19]

McCaman et al.

[11] Patent Number: 5,082,775

[45] Date of Patent: Jan. 21, 1992

[54] EFFICIENT PROCESS FOR ISOLATING INSOLUBLE HETEROLOGOUS PROTEIN USING NON-IONIC DETERGENTS

[75] Inventors: Michael T. McCaman, San Bruno; John F. King, San Francisco, both of Calif.

[73] Assignee: Berlex Laboratories, Inc., Cedar Knolls, N.J.

[21] Appl. No.: 263,927

[22] Filed: Oct. 28, 1988

Related U.S. Application Data

[63] Continuation-in-part of Ser. No. 856,700, Apr. 28, 1986, which is a continuation-in-part of Ser. No. 480,860, Mar. 31, 1983, abandoned, and a continuation-in-part of Ser. No. 940,199, Dec. 12, 1986, which is a continuation-in-part of Ser. No. 609,495, May 11, 1984, abandoned.

[51] Int. Cl.$^5$ ............... C12N 1/21; C12N 15/00; C12N 9/64; C12N 9/80; C12P 21/00; A61K 37/54; C07K 7/00

[52] U.S. Cl. ............... 435/69.7; 435/172.3; 435/320.1; 435/226; 435/228; 435/252.33; 424/94.66; 935/72; 935/73; 530/412

[58] Field of Search ............ 435/68, 172.3, 320, 435/226, 268; 424/94, 66; 530/412

[56] References Cited

U.S. PATENT DOCUMENTS

| | | |
|---|---|---|
| 2,145,796 | 1/1939 | Keil . |
| 2,376,848 | 5/1945 | Hankinson . |
| 2,506,877 | 8/1946 | Keil . |
| 3,151,039 | 9/1964 | Arima . |
| 3,281,332 | 10/1966 | Munns et al. . |
| 3,616,233 | 10/1971 | Schleich . |
| 3,950,221 | 4/1976 | Kokusho et al. . |
| 4,081,330 | 3/1978 | Horisberger . |
| 4,136,201 | 1/1979 | Feldman . |
| 4,366,246 | 12/1982 | Riggs . |
| 4,511,502 | 4/1985 | Builder . |
| 4,511,503 | 4/1985 | Olson . |
| 4,512,922 | 4/1985 | Jones . |
| 4,518,526 | 5/1985 | Olson . |
| 4,526,868 | 7/1985 | Shasuzzaman . |
| 4,599,197 | 7/1986 | Wetzel . |
| 4,620,948 | 11/1986 | Builder . |
| 4,721,673 | 1/1988 | Uren et al. . |

FOREIGN PATENT DOCUMENTS

| | | |
|---|---|---|
| 0001930 | 5/1979 | European Pat. Off. . |
| 2091271A | 7/1982 | European Pat. Off. . |
| 0057350 | 8/1982 | European Pat. Off. . |
| 0068691 | 1/1983 | European Pat. Off. . |
| 2100737A | 1/1983 | European Pat. Off. . |
| 0073029 | 3/1983 | European Pat. Off. . |
| 0077109 | 4/1983 | European Pat. Off. . |
| 0121775 | 10/1984 | European Pat. Off. . |
| 0134662 | 3/1985 | European Pat. Off. . |
| 0154351 | 9/1985 | European Pat. Off. . |
| WO83/04418 | 12/1983 | PCT Int'l Appl. . |

OTHER PUBLICATIONS

Dennis G. Kleid, et al., "Cloned Viral Protein Vaccine for Foot-and-Mouth Disease: Responses in Cattle and Swine," *Science*, vol. 214, pp. 1125–1128 (4 Dec. 1981).

Emtage et al., "Synthesis of calf prochymosin (prorennin) in Escherichia coli," *Proc. Natl. Acad. Sci.*, 80:3671–3675 (1983).

Nishimori et al., "Expression of cloned calf prochymosin cDNA under control of the tryptophan promoter," *Gene* 29:41–49 (1984).

Goff et al., "Expression of calf prochymosin in Saccharomyces cerevisiae," *Gene* 27:35–46 (1984).

(List continued on next page.)

*Primary Examiner*—Elizabeth C. Weimar
*Assistant Examiner*—Christopher Low
*Attorney, Agent, or Firm*—Townsend and Townsend

[57] ABSTRACT

The present invention relates to the isolation and restoration of biological activity to inactive proteins, that is solubilizing, renaturing and restoring activity to proteins which have been partially denatured or inactivated, e.g. during their synthesis in a host cell, such as *E. coli*, or during isolation. In particular this invention relates to both a means for extracting insoluble eukaryotic proteins from bacteria and to an efficient process for producing active chymosin from an insoluble chymosin precursor isolated from genetically engineered bacteria.

5 Claims, 9 Drawing Sheets

Mellor et al., "Efficient synthesis of enzymatically active calf chymosin in Saccharomyces cerevisiae," *Gene* 24:1-14 (1983).

Foltmann et al., "The Primary Structure of Calf Chymosin," *J. Biol. Chem.* 254:8447-8456 (1983).

Berridge, N. J., "Rennin and the Clotting of Milk," *Advances in Enzymology*, vol. XV:423-425 (1954).

Kahn et al., "Plasmid Cloning Vehicles Derived from Plasmids ColE1, F, R6K, and RK2," *Methods in Enzymology*, 68:268-273 (1979).

Messing et al., "A system for shotgun DNA sequencing," *Nucleic Acids Research*, 9:309-320 (1981).

Harris et al., "Molecular cloning and nucleotide sequence of cDNA coding for calf preprochymosin," *Nucleic Acids Research*, 10:2177-2187 (1982).

Moir et al., "Molecular cloning and characterization of double stranded cDNA coding for bovine chymosin," *Gene*, 19:127-138 (1982).

Nishimori et al., "Cloning in Escherichia coli of the Structural Gene of Prorennin, the Precursor of Calf Milk-Clotting Enzyme Rennin," *J. Biochem.*, 90:901-904 (1981).

Nishimori et al., "Nucleotide Sequence of Calf Prorennin cDNA Cloned in Escherichia coli," *J. Biochem.*, 91:1085-1088 (1982).

Windholz et al., eds., *The Merck Index*, 10ed., p. 971 (1983).

Uchiyama et al., "Purification of Prorennin mRNA and Its Translation in Vitro," *Agric. Biol. Chem.*, 44:1373-1381 (1980).

Uchiyama et al., "Purification of Prorennin and Production of Its Antibody," *J. Biochem.*, 90:483-487 (1981).

Wetzel et al., "Production of Biologically Active N-Desacetylthymosin a1 in Escherichia coli through Expression of a Chemically Synthesized Gene," *Biochem.*, 19:6096-6104 (1980).

Wetzel et al., "Expression in Escherichia coli of a chemically synthesized gene for a mini-C analog of human proinsulin," *Gene*, 16:63-71 (1981).

Mahler, H. R. and Cordes, E. H., *Biological Chemistry*, 2nd ed. Harper and Row, Publishers, New York, pp. 177-183 (1971).

Nishimori et al., "Expression of cloned calf prochymosin gene sequence in Escherichia coli," *Gene*, 19:337-344 (1982).

Gerhardt et al. (eds.), 1981 in: *Manual of Methods for General Bacteriology*, Am. Soc. for Microbiol., Washington, D.C., pp. 52-61.

Garewal et al., 1974 Biochemistry 13, 1063-1071.

Prouty et al., 1975, J. Biol. Chem., 250, 1112-1122.

Scopes, R. K., 1982, in: *Protein Purification, Principles and Practice*, Springer-Verlag, New York, p. 37.

Cooper, T. G., in *The Tools of Biochemistry*, John Wiley & Sons, New York, p. 363.

Signo Catalog, 1990, p. 1500.

Encyclopedia of Chemical Technology, 1983, vol. 22, pp. 332-432, John-Wiley & Sons, New York.

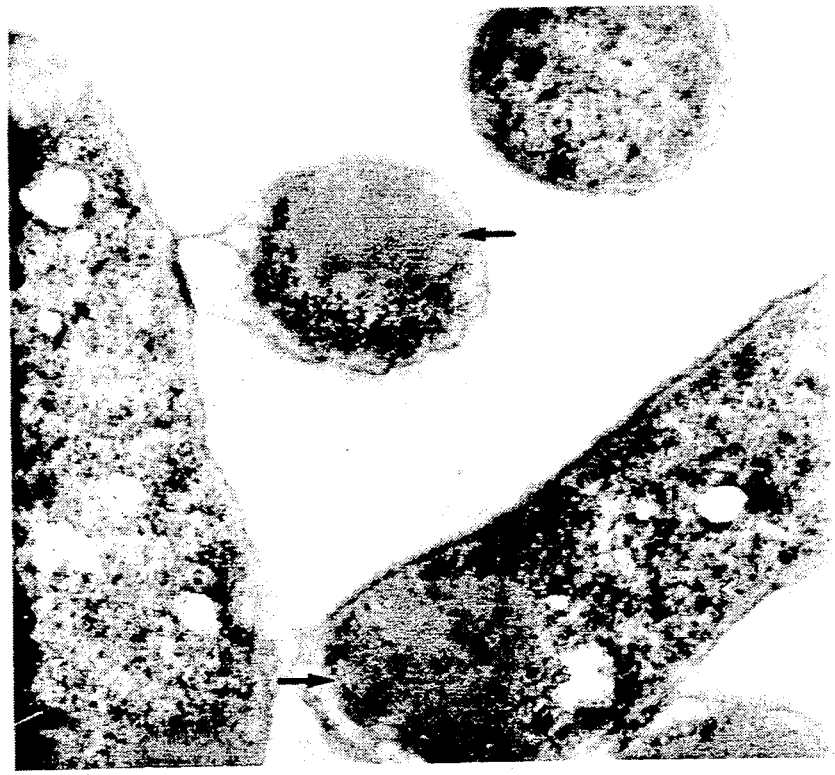
FIG._IA.
FIG._IB.

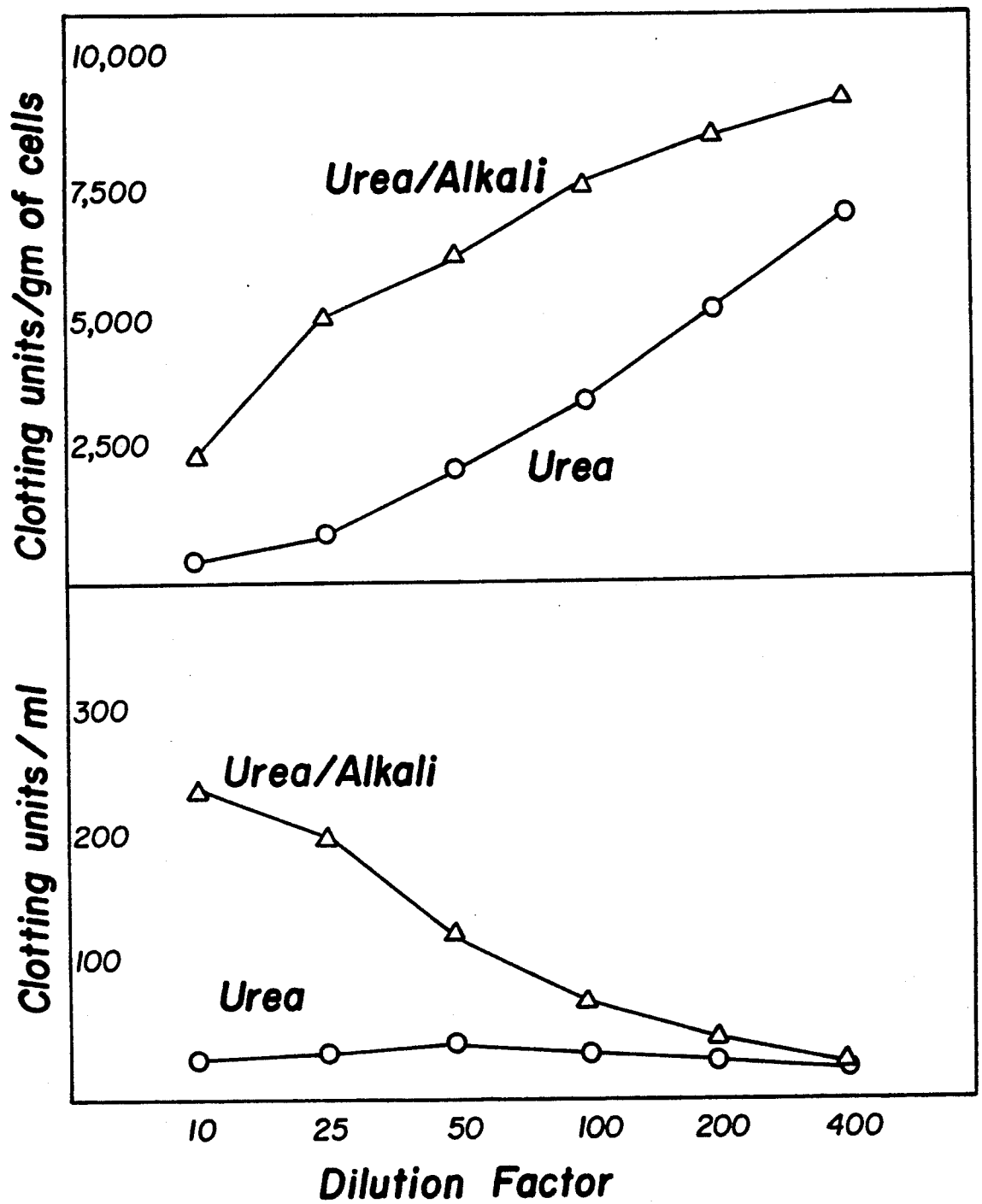
FIG._2.

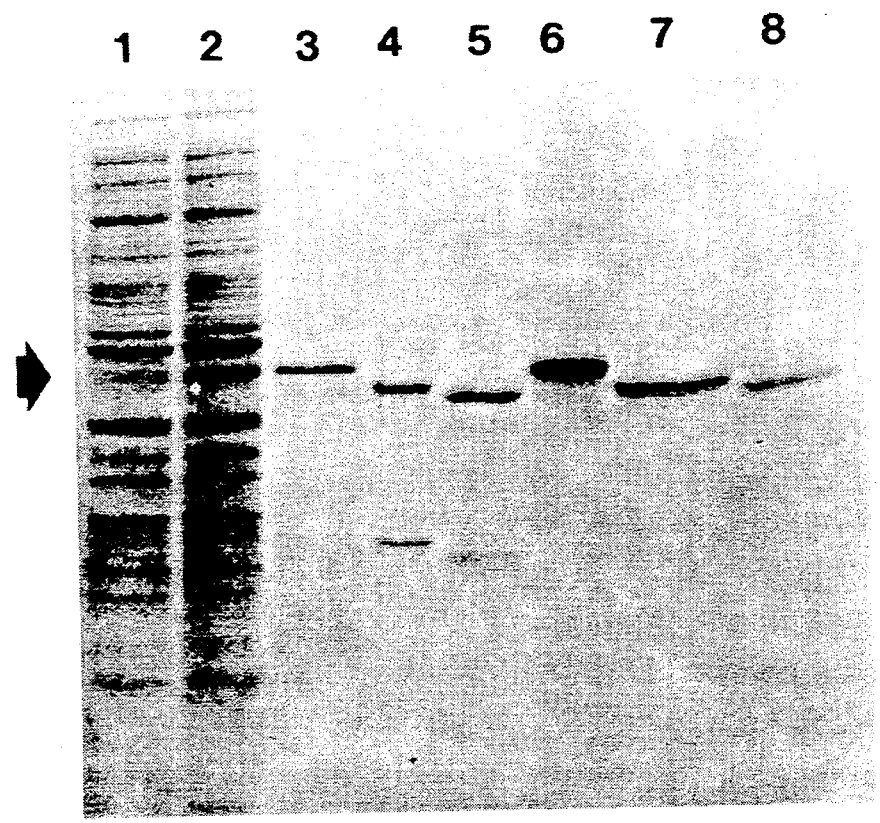
FIG._3.

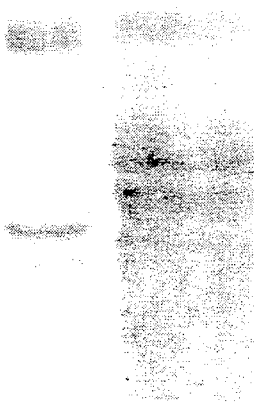
FIG._4.

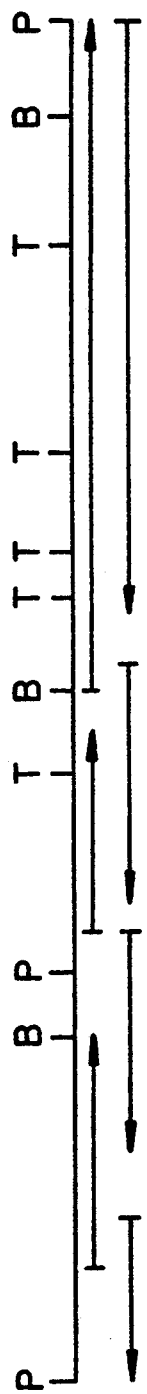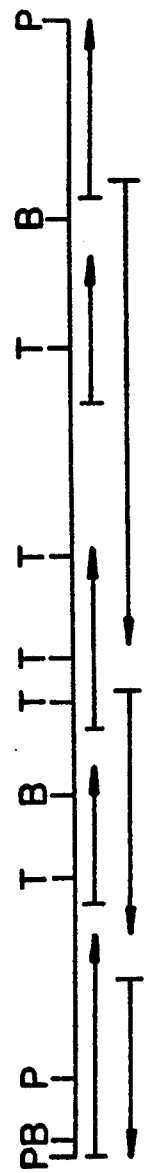
Fig. 5a.
Fig. 5b.

```
CGGCUGGACC CAGAUCCAAG AUG AGG UGU CUC GUG GUG CUA CUU GCU GUC
                     Met Arg Cys Leu Val Val Leu Leu Ala Val
                     -16                     -10

UUC GCU CUC UCC CAG GGC GCU GAG AUC ACC AGG AUC CCU CUG UAC AAA
Phe Ala Leu Ser Gln Gly Ala Glu Ile Thr Arg Ile Pro Leu Tyr Lys
                        1                                    10

GGC AAG UCU CUG AGG AAG GCG CUG AAG GAG CAU GGG CUU CUG GAG GAC
Gly Lys Ser Leu Arg Lys Ala Leu Lys Glu His Gly Leu Leu Glu Asp
                            20

UUC CUG CAG AAA CAG CAG UAU GGC AUC AGC AGC AAG UAC UCC GGC UUC
Phe Leu Gln Lys Gln Gln Tyr Gly Ile Ser Ser Lys Tyr Ser Gly Phe
            30                                  40

GGG GAG GUG GCC AGC GUG CCC CUG ACC AAC UAC CUG GAU AGU CAG UAC
Gly Glu Val Ala Ser Val Pro Leu Thr Asn Tyr Leu Asp Ser Gln Tyr
                        50

UUU GGG AAG AUC UAC CUC GGG ACC CCG CCC CAG GAG UUC ACC GUG CUG
Phe Gly Lys Ile Tyr Leu Gly Thr Pro Pro Gln Glu Phe Thr Val Leu
    60                                  70

UUU GAC ACU GGC UCC UCU GAC UUC UGG GUA CCC UCU AUC UAC UGC AAG
Phe Asp Thr Gly Ser Ser Asp Phe Trp Val Pro Ser Ile Tyr Cys Lys
                        80                                   90

AGC AAU GCC UGC AAA AAC CAC CAG CGC UUC GAC CCG AGA AAG UCG UCC
Ser Asn Ala Cys Lys Asn His Gln Arg Phe Asp Pro Arg Lys Ser Ser
                            100

ACC UUC CAG AAC CUG GGC AAG CCC CUG UCU AUC CAC UAC GGG ACA GGC
Thr Phe Gln Asn Leu Gly Lys Pro Leu Ser Ile His Tyr Gly Thr Gly
            110                                 120

AGC AUG CAG GGC AUC CUA GGC UAU GAC ACC GUC ACU GUC UCC AAC AUU
Ser Met Gln Gly Ile Leu Gly Tyr Asp Thr Val Thr Val Ser Asn Ile
                        130

GUG GAC AUC CAG GAG ACA GUA GGC CUG AGC ACC CAG GAG CCC GGG GAC
Val Asp Ile Gln Glu Thr Val Gly Leu Ser Thr Gln Glu Pro Gly Asp
    140                                 150

GUC UUC ACC UAU GCC GAA UUC GAC GGG AUC CUG GGG AUG GCC UAC CCC
Val Phe Thr Tyr Ala Glu Phe Asp Gly Ile Leu Gly Met Ala Tyr Pro
                        160                                 170

CCC UCG CUC GCC UCA GAG UAC UCG AUA CCC GUG UUU GAC AAC AUG AUG
Pro Ser Leu Ala Ser Glu Tyr Ser Ile Pro Val Phe Asp Asn Met Met
                                180
```

FIG. 6.

```
AGG CAC CUG GUG GCC CAA GAC CUG UUC UCG GUU UAC AUG GAC AGG AAU
Arg His Leu Val Ala Gln Asp Leu Phe Ser Val Tyr Met Asp Arg Asn
            190                                     200

GGC CAG GAG AGC AUG CUC ACG CUG GGG GCC AUC GAC CCG UCC UAC UAC
Gly Gln Glu Ser Met Leu Thr Leu Gly Ala Ile Asp Pro Ser Tyr Tyr
                        210

ACA GGG UCC CUG CAC UGG GUG CCC GUG ACA GUG CAG CAG UAC UGG CAG
Thr Gly Ser Leu His Trp Val Pro Val Thr Val Gln Gln Tyr Trp Gln
    220                                         230

UUC ACU GUG GAC AGU GUC ACC AUC AGC GGU GUG GUU GUG GCC UGU GAC
Phe Thr Val Asp Ser Val Thr Ile Ser Gly Val Val Val Ala Cys Glu
                    240                                     250

GGU GGC UGU CAG GCC AUC CUG GAC ACG GGC ACC UCC AAG CUG GUC GGG
Gly Gly Cys Gln Ala Ile Leu Asp Thr Gly Thr Ser Lys Leu Val Gly
                                260

CCC AGC AGC GAC AUC CUC AAC AUC CAG CAG GCC AUU GGA GCC ACA CAG
Pro Ser Ser Asp Ile Leu Asn Ile Gln Gln Ala Ile Gly Ala Thr Gln
            270                                     280

AAC CAG UAC GAU GAG UUU GAC AUC GAC UGC GAC AAC CUG AGC UAC AUG
Asn Gln Tyr Asp Glu Phe Asp Ile Asp Cys Asp Asn Leu Ser Tyr Met
                        290

CCC ACU GUG GUC UUU GAG AUC AAU GGC AAA AUG UAC CCA CUG ACC CCC
Pro Thr Val Val Phe Glu Ile Asn Gly Lys Met Tyr Pro Leu Thr Pro
    300                                         310

UCC GUU UAU ACC AGC CAA GAC CAG GGC UUC UGU ACC AGU GGC UUC CAG
Ser Val Tyr Thr Ser Gln Asp Gln Gly Phe Cys Thr Ser Gly Phe Gln
                    320                                     330

AGU GAA AAU CAU UCC CAG AAA UGG AUC CUG GGG GAU GUU UUC AUC CGA
Ser Glu Asn His Ser Gln Lys Trp Ile Leu Gly Asp Val Phe Ile Arg
                                340

GAG UAU UAC AGC GUC UUU GAC AGG GCC AAC AAC CUC GUG GGG CUG GCC
Glu Tyr Tyr Ser Val Phe Asp Arg Ala Asn Asn Leu Val Gly Leu Ala
            350                                     360

AAA GCC AUC UGA UCACACCCC
Lys Ala Ile OP
            365
```

FIG. 6.

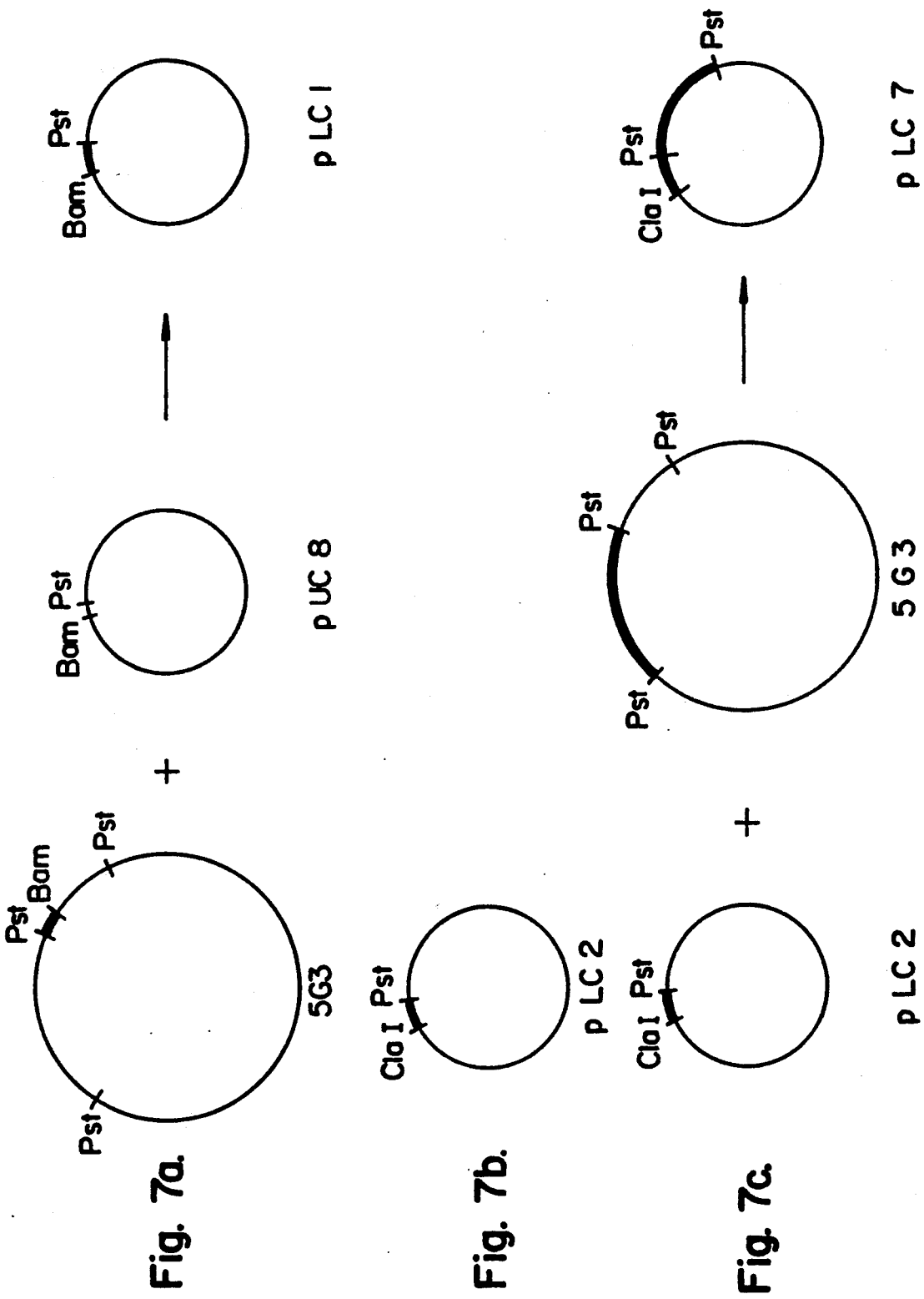

```
AAUUGUGAGC GGAUAACAAU UUCACACAGG AAACAGGAAA CAGCU AUG ACC AUG
                                                  Met Thr Met

AUU ACG AAU UCC CGG GGA UCG AUC CCU CUG UAC AAA GGC AAG UCU CUG
Ile Thr Asn Ser Arg Gly Ser Ile Pro Leu Tyr Lys Gly Lys Ser Leu
                            6                10

AGG AAG GCG CUG AAG GAG CAU GGG CUU CUG GAG GAC UUC CUG CAG AAA
Arg Lys Ala Leu Lys Glu His Gly Leu Leu Glu Asp Phe Leu Gln Lys
                    20                                       30

CAG CAG UAU GGC AUC AGC AGC AAG UAC UCC GGC UUC
Gln Gln Tyr Gly Ile Ser Ser Lys Tyr Ser Gly Phe
                                    40
```

FIG._8.

EFFICIENT PROCESS FOR ISOLATING INSOLUBLE HETEROLOGOUS PROTEIN USING NON-IONIC DETERGENTS

This application is a continuation-in-part of U.S. Application Ser. No. 856,700, filed Apr. 28, 1986, which was a continuation of U.S. Ser. No. 480,860, filed Mar. 31, 1983 (abandoned), and is a continuation-in-part of U.S. Serial No. 940,199, filed Dec. 12, 1986, which was a continuation of U.S. Application Ser. No. 609,495, filed May 11, 1984 (abandoned).

TECHNICAL FIELD OF INVENTION

The present invention relates to the isolation and restoration of biological activity to inactive proteins, that is solubilizing, renaturing and restoring activity to proteins which have been partially denatured or inactivated, e.g. during their synthesis in a host cell, such as E. coli or during isolation. In particular this invention relates to both a means for extracting insoluble eukaryotic proteins from bacteria and to an efficient process for producing active chymosin from an insoluble chymosin precursor isolated from genetically engineered bacteria.

This invention also relates to the clotting of milk, used as a step in the process of making of cheese. More specifically the invention relates to the synthesis using recombinant DNA techniques of a polypeptide derived from calf rennin which displays milk-clotting activity.

BACKGROUND OF THE INVENTION

With the advent of recombinant DNA technology, it is now possible to introduce foreign genes into microorganisms and regulate the level of their expression.

However, the synthesis of an excess of polypeptide or protein not endogenous to the bacterium may have an adverse effect on the organism's viability, especially if produced at a high level relative to other host proteins. In some instances, the host organism may have a mechanism of disposing of the cloned gene product, e.g. by degrading it or secreting it, thus avoiding interaction with the essential metabolic machinery of the cell. Alternatively, the cloned gene product may assume an altered conformation, thus limiting its interference with normal cellular processes. Disruption or alteration of normal translational or post-translational events, the specific codon usage pattern during protein synthesis, and/or host protein-cloned gene product interactions within the cell, may also effect the polypeptide's normal folding and assembly and may result in an inactive conformation of the protein. In a host organism such as E. coli it has been observed in several cases that foreign proteins fold unnaturally and precipitate within the cell to form large inactive protein aggregates, characterized as inclusion bodies (Williams, D.C., et al. Science 215:687–689 (1982) and Kleid, D.G., et al. Science 214:1 125–1128 (1981).

Purification schemes for recombinant proteins generally involve physical isolation (extraction) of insoluble heterologous proteins followed by biological or immunological activation. Extraction of the insoluble fraction can be achieved in a number of ways, typically by differential centrifugation. Typically such means result in concomitant containment of the insoluble protein with proteins and membranous debris originating from the host cells.

It has been shown that native (active) proteins can undergo reversible denaturation (Anfinsen, C., Science 181:223–230 (1973) and London, J. et al., Eur. J. Biochemistry 47:409–415 (1974). The protein is denatured by addition of 8 molar urea and polypeptide refolding occurs spontaneously as the urea is removed. Alkali solutions have also been used as protein solubilizing agents and in some cases can reversibly denature native proteins during brief incubation times (McPhie, P.J. of Biol. Chem 257:689–693 (1982).

Urea has also been used to aid in the renaturation of the gene product of a recombinant DNA expression system (Emtage, J.S. et al., Proc. Nat. Acad. Sci. USA 80:3671–3675 (1983)).

This invention also relates to Rennin, also known as chymosin (EC3.4.23.4). Rennin is the active component of rennet which is used to clot milk in the process of making cheese. Commercial preparations of calf rennet are obtained from the mucosal lining of the fourth stomach of unweaned calves (the abomasum). A reduction in the current veal market and subsequent increase in cheese consumption has forced the dairy industry to find substitutes for calf rennet. In fact there is only enough calf rennet to supply 20% of the cheese market.

Proteinases isolated from fungi have been employed in conjunction with or as a substitute for bovine rennet. See for example U.S. Pat. Nos. 3,151,039 and 3,212,905. However, these aspartate proteinases have a broader substrate range and are more stable during the milk-clotting process. This increase in proteolytic activity and stability can alter the flavor and texture of the final cheese product. Moreover, losses of protein during cheese making are often greater with rennet substitutes, causing a lower yield. In order to provide the dairy industry with an enzyme preparation which is a polypeptide derived from authentic bovine rennet and purified from a non-animal source, recombinant DNA techniques have been utilized.

Bovine rennin is synthesized in two active forms, chymosin-A and chymosin-B, which differ only in a single amino acid at position #290. Rennin is synthesized as a precursor which contains a signal peptide of 16 amino acids. Harris, T.J.R., et al., Nucl. Acids Res. 10:2177-87 (1982); Moir, D., et al., Gene, 19:127-38 (1982). This signal peptide is cleaved as the protein is secreted from the cell. Once secreted the zymogen, called prorennin, undergoes activation under the acidic conditions of the stomach to generate mature rennin. The activation is apparently autocatalytic and may occur in stages. (B. Foltmann, Trav. Lab. Carlsberg, 35:143-231 (1966)). Within prorennin two peptide bonds can be cleaved autocatalytically, the Phe-Leu bond between amino acids 28 and 29, and the Phe-Gly bond between amino acids 42 and 43. In vitro studies have indicated that at pH 2 the first bond is preferentially cleaved to generate pseudorennin, while at pH 4.7 the second bond is cleaved to generate mature rennin. Both forms of rennin are active in clotting milk.

Attempts have been made to produce authentic rennin by recombinant DNA means. See, e.g. Alford, B.L. et al., European Patent Application Serial No. 82100124.5 filed January 8, 1982. However, the methods require complicated construction strategies to complete the rennin structural gene, and suffer from low efficiency of expression. Thus it is an object of this invention to provide an active polypeptide which can be used by the dairy industry as a substitute for bovine rennin.

It is a further object of this invention to provide living cells containing recombinant DNA material which synthesizes with high efficiency a polypeptide having milk- clotting activity.

It is a still further object of this invention to provide alternative recombinant DNA which may be adapted to particular host cell cultures.

It is another object of this invention to provide DNA sequences derived from bovine rennin which code for polypeptides having milk-clotting activity.

It is another object of this invention to provide methods for synthesis of polypeptides specified by DNA sequences derived from bovine rennin in a bacterial cell.

It is another object of this invention to provide methods for recovery of polypeptides which are synthesized in bacterial cells containing DNA sequences derived from bovine rennin and which are able to clot milk.

It is still another object of this invention to provide methods of constructing recombinant DNA incorporating DNA sequences derived from bovine rennin.

It is yet another object of this invention to provide methods of clotting milk using polypeptides having milk-clotting activity which are synthesized from DNA sequences derived from bovine rennin.

SUMMARY OF THE INVENTION

The present invention provides a process for extracting and producing active chymosin from an insoluble chymosin precursor protein comprising solubilizing said protein in a solubilizing reagent capable of so solubilizing the protein and removing the reagent whereby the protein assumes a thermodynamically stable and biologically active conformation. Characteristically, the protein which is isolated from its host cell, e.g.. *E. coli*, differs in its physical and chemical characteristics from the same protein isolated from its natural environment (calf stomach prochymosin). The same physical and chemical characteristics of the isolated protein are caused to duplicate those of the naturally occurring product by practicing the present invention, that is, by solubilizing the inactive or denatured gene product in a suitable solubilizing reagent and removing the reagent in a manner which allows the polypeptide to assume a thermodynamically stable form possessing its natural biological activity.

An aspect of the present invention discloses novel processes for producing active chymosin, utilizing nonionic detergents (Triton X-100) as a reagent for protein purification and urea and alkali as reagents for solubilization and renaturation. Thus the present invention is a novel and original procedure for protein renaturation.

In addition to the above processes, there is also disclosed herein methods and compositions for synthesizing within a bacterial host a polypeptide which displays milk-clotting activity. According to a method of this invention, recombinant DNA may be constructed which includes a structural gene which codes for a polypeptide displaying milk-clotting activity. In this method a DNA sequence which codes for said polypeptide is derived from bovine sources, and inserted into a cloning vector with a promoter and ribosomal binding site upstream from the DNA sequence. This recombinant DNA is then used to transform a bacterial host and the host is cultured under conditions which promote expression of the polypeptide.

Also in accordance with this invention, compositions are provided which are capable of synthesizing a polypeptide displaying milk-clotting activity. Using the methods and compositions provided in this invention, a polypeptide is obtained which displays milk-clotting activity and which may be synthesized at high levels of efficiency in a host cell system.

More particularly, there is disclosed herein a process for isolating a substantially insoluble polypeptide being produced by a genetically engineered organism which does not naturally produce said gene product (heterologous), the process comprising the steps of: (a) contacting said polypeptide with a solution containing a nonionic detergent at a concentration sufficient to solubilize impurities while maintaining the insolubility of the polypeptide; and (b) separating the insoluble protein from the soluble impurities. It is preferrred that the organism is a bacterium such as *Escherichia coli*. The preferred nonionic detergent is Triton X-100.

There is also described herein a process for converting a substantially insoluble polypeptide, said polypeptide being produced by a genetically engineered organism which does not naturally produce said polypeptide in either biologically active or inactive form, to a biologically active soluble polypeptide, polypeptide, the process comprising isolation steps of: (a) obtaining a bacterial lysate containing said polypeptide; (b) contacting said insoluble polypeptide by treating said bacterial lysate with a non-ionic detergent solution; (c) separating the insoluble polypeptide from the soluble impurities; (d) solubilizing said polypeptide from step c in a solubilizing reagent capable of denaturing said polypeptide, said solubilizing reagent being selected from a chaotropic reagent, an alkaline solution having a pH of approximately 11.0 or greater, or a combination thereof; and (e) renaturing said denatured polypeptide to form a biologically active gene product by reducing the influence of the solubilizing reagent.

More specifically there is also disclosed herein a method of synthesizing and purifying a polypeptide selected from chymosin, precursors of chymosin and fusion products thereof capable of displaying milk clotting activity, wherein a bacterial host containing recombinant DNA capable of expressing a DNA sequence which codes for said polypeptide is cultured under conditions which allow the expression of said polypeptide in an insoluble state from said DNA sequence and thereafter the polypeptide is extracted from the lysed bacterial host, the improvement comprising: (a) purifying the polypeptide by contacting the bacterial lysate with at least one detergent for a time and under conditions sufficient to solubilize bacterial material associated with insoluble polypeptide; (b) removing the detergent and the solubilized material from the insoluble polypeptide; and (c) solubilizing the polypeptide by contacting the insoluble polypeptide with at least one protein denaturing agent and subsequently removing said protein denaturing agent under conditions which allow said polypeptide to renature. It is preferred that the detergent be a non-ionic detergent such as Triton X-100 and that at least one protein denaturing agent comprises urea. Naturation of the protein is preferably achieved by decreasing the concentration of the protein denaturing agent at basic pH to a level sufficient to permit the polypeptide to renature into the native conformation.

The process described above may also comprise the step of contacting the purified and renatured polypeptide with a medium having an acidic pH value for times and under conditions sufficient to produce a polypeptide which displays milk clotting activity. Alternatively, the process may also comprise the step of contacting the purified and renatured polypeptide with a medium containing at least one protease capable of activating said polypeptide for times and under conditions sufficient to produce a polypeptide which displays milk clotting activity.

In a second context there is disclosed herein a method of synthesizing and purifying a polypeptide especially a polypeptide selected from the group comprising chymosin, precursors of chymosin, and fusion products thereof capable of displaying milk clotting activity, wherein a bacterial host containing recombinant DNA capable of expressing a DNA sequence which codes for said polypeptide is cultured under conditions which allow the expression of said polypeptide in an insoluble state from said DNA sequence, and thereafter, the polypeptide is extracted from the lysed bacterial host, the improvement comprising: solubilizing the polypeptide by contacting the insoluble polypeptide with at least one protein denaturing agent and subsequently removing said protein denaturing agent under conditions which allow said polypeptide to renature. It is preferred that the solubilizing agents comprise a chaotropic agent and an alkali. Preferred alkali are sodium hydroxide and potassium hydroxide. The preferred chaotropic agent is urea.

This invention is also particularly directed to a method of clotting milk comprising: (a) providing a medium containing milk or components of milk; (b) providing a polypeptide selected from chymosin, precursors of chymosin and fusion products thereof capable of displaying milk clotting activity, wherein a bacterial host containing recombinant DNA capable of expressing a DNA sequence which codes for said polypeptide is cultured under conditions which allow the expression of said polypeptide in an insoluble state from said DNA sequence and thereafter the polypeptide is extracted from the lysed bacterial host, said polypeptide being produced by the process comprising the steps of: (c) purifying the polypeptide by contacting the bacterial lysate with at least one detergent for a time and under conditions sufficient to solubilize bacterial material associated with insoluble polypeptide; (d) removing the detergent and the solubilized material from the insoluble polypeptide; (e) solubilizing the polypeptide by contacting the insoluble polypeptide with at least one protein denaturing agent and subsequently removing said protein denaturing agent under conditions which allow said polypeptide to renature; and (f) contacting the purified and renatured polypeptide with a medium sufficient to produce a polypeptide which displays milk clotting activity; and contacting said medium containing said milk or components of milk with said polypeptide. It is preferred that this process further comprise a medium having an acidic pH value for times and under conditions sufficient to produce a polypeptide which displays milk clotting activity. It is also useful for the milk clotting activity producing medium to include a protease capable of activating said polypeptide for times and under conditions sufficient to produce a polypeptide which displays milk clotting activity.

This invention is also directed to enzymatically active chymosin produced by processes described above.

This invention is further directed to recombinant DNA which is capable of directing synthesis of a polypeptide displaying milk-clotting activity and which comprises: (a) a DNA sequence which is capable of autonomous replication in a bacterial host and which further comprises: (1) a bacterial promoter sequence; followed by (2) a translation start signal; followed by (3) amino acid codons; followed by (4) a non-bacterial DNA sequence aligned with the translation start signal reading frame and coding for a polypeptide which displays milk-clotting activity. More specifically there is described a recombinant DNA as described above wherein said non-bacterial DNA sequence essentially corresponds to the RNA nucleotide sequence as shown in FIG. 6. The recombinant DNA may optionally code for a fusion peptide such as the one which corresponds to the DNA nucleotide sequence essentially as shown in FIG. 7. More particularly this invention is embraced in the the recombinant DNA material contained in *E. coli* strain JM 83/pLC7 as deposited on Mar. 28, 1983 in the ATCC which is identified as Accession No. 39325.

The polypeptides of this invention include those capable of displaying milk-clotting activity comprising the expression product of the recombinant DNA sequences described above with the polypeptide comprising the amino acid sequence essentially as shown in FIG. 6. More specifically the polypeptides of this invention are available from the culturing of the E. coli strain desposited as ATCC No. 39325. The peptides of this invention are activated by exposure to a medium having a pH value of 2 and or a pH of 4.5 substantially in an order that said polypeptide displays milk-clotting activity.

BRIEF DESCRIPTION OF THE FIGURES

FIG. 1 shows an electron micrograph cross-section of E. coli cells (1A) containing prochymosin inclusion bodies (arrows) and (B) wild type bacteria which do not contain inclusion bodies.

FIG. 2 shows the recovery of milk-clotting activity derived from pWHA49 prochymosin after solubilization and renaturation by two of the processes disclosed in this invention. The observed activity per volume is plotted against the dilution factor (material from 1 gram of cell paste/final volume in mls) at which the renaturation reaction was performed.

FIG. 3 shows a polyacrylamide gel containing protein samples derived from *E. coli* synthesizing prochymosin, wherein the samples include: total cell proteins from parental *E. coli* strain CY15001 (lane 1); total cell proteins from prochymosin expression strain CY15001/pWHA49 (lane 2); purified and renatured pWHA49 prochymosin after pH 2.0 activation (lane 4); purified and renatured pWHA49 prochymosin after pH 4.5 activation (lane 5); purified calf prochymosin (lane 6); purified calf prochymosin after activation at pH (lane 7); and purified calf prochymosin after activation at pH 4.5 (lane 8).

FIG. 4 shows a polyacrylamide gel containing protein samples derived from a milk substrate before and after reaction with chymosin derived from either calf or pWHA49 prochymosin, wherein the samples include: molecular weight markers (lane 1); unreacted milk substrate (lane 2); milk coagulated with pWHA49 pseudochymosin (lane 3); milk coagulated with pWHA49 chymosin (lane 4); milk coagulated with calf chymosin (lane 5); and milk substrate coagulated with trypsin (lane 6). The arrow indicates K-casein protein component cleaved by chymosin to initiate coagulation reaction.

FIG. 5a and 5b displays the restriction enzyme maps of two DNA fragments obtained by reverse transcriptase treatment of bovine mRNA and which code for a polypeptide displaying milk- clotting activity.

FIG. 6 shows the nucleotide sequence and amino acid sequence for prochymosin.

FIG. 7a, 7b, and 7c, together schematically show the method used in section 8 for inserting a DNA fragment as described in FIG. 6 into an appropriate expression vector derived from plasmid pBR322.

FIG. 8 shows the DNA nucleotide sequence coding for a fusion peptide and including the promoter sequence, amino acid codons and rennin-derived codons through codon 42. FIG. 7 also shows the corresponding amino acid sequence where appropriate.

DETAILED DESCRIPTION OF THE INVENTION

The present invention provides methods and compositions to generate a polypeptide having milk-clotting activity, using recombinant DNA technology. Sequences coding for bovine rennin were isolated from stomach tissue, transcribed into cDNA, and cloned into a bacterial cloning vector. The nucleotide sequences were then transferred into specially designed expression plasmids in order to maximize synthesis of the polypeptide. After purification, in vitro conditions of the calf stomach were duplicated to acid activate the synthetic rennin polypeptide.

Stomachs from unweaned calves were selected for mRNA isolation because this tissue produces in vivo the highest levels of active rennin. Reverse transcriptase was used to transcribe mRNA into a cDNA copy to be cloned in bacteria. However, reverse transcriptase is prone to premature termination of transcription; hence, a size selection was carried out to enrich for full length gene copies. Two clones were analyzed in detail. One contained the entire coding region for the A form of rennin, while the other contained all the sequences of the mature A form of rennin but lacked sequences from the N-terminal cleavage fragment of prorennin. The second clone also contains sequences from the 3'-untranslated region proceeding the poly-A tail.

With these two rennin clones, the DNA sequences were rearranged in order to maximize their expression. The cloned DNA fragments are like "cassettes" that can be inserted into a variety of specially constructed expression vectors. It is necessary to build into a efficient expression vector a strong promoter for RNA polymerase and an effective ribosome binding site to initiate protein synthesis. With the use of specific restriction endonucleases, it is possible to insert the DNA sequence into a bacterial expression plasmid so that the structural gene for calf rennin can be transcribed in response to the bacterial promoter.

The polypeptide is synthesized in bacterial cells at high levels. However, the purification of the polypeptide is complicated by its tendency to aggregate and sediment with bacterial membranes. When the polypeptide is purified with bacterial membranes, it is not active. Activity can be restored by extraction of the polypeptide from membrane components with urea. Treatment with urea apparently denatures the polypeptide molecules which can then refold into an active conformation, and enzyme activity can be measured following acid activation.

The present invention is also directed to an advantageous means to produce active chymosin from a chymosin precursor protein isolated in an insoluble, inactive and/or partially denatured state from E. coli (see FIG. 1). The term "denatured" is intended to describe the form of the protein whose conformation and biological activity differs significantly from the same protein isolated from its natural environment. the details of the process are described below. A bacterial cell paste is resuspended in a buffer containing lysozyme and as cell lysis occurs the viscosity of the solution increases due to the bacterial DNA. For the present invention, it is important to reduce the viscosity of the lysate by physical methods such as sonic disruption of the DNA or use of a French press. The insoluble fraction of the cell is isolated by low speed centrifugation. The insoluble fraction is resuspended in buffer and mixed with a solution containing a non-ionic detergent (Triton X-100) for 2–20 hours. This detergent does not solubilize the chymosin precursor protein but does solubilize other bacterial protein contaminants. These contaminants are separated and removed from the insoluble chymosin precursor protein by centrifugation. The insoluble fraction is solubilized in 8M urea for 2–20 hours, preferably 10–16 hours and then diluted into an alkaline phosphate buffer preferably pH 10.5–11.5, and most preferably pH 11.0, incubated for 5–30 minutes, most preferably 10 minutes, and then neutralized slowly to a pH of 8–9, preferably 8.3 and allowed to stand for one hour or more. Subsequent acidification to a pH less than 5 resulted in the generation of a milk-clotting activity whose properties are the same as calf stomach chymosin.

The present invention requires several specific steps to achieve efficient recoveries of active chymosin. First, the combination of sonication (after cell lysis) and Triton X-100 extraction (after collecting the insoluble proteins by centrifugation) are essential to this process.

Table I, infra, illustrates the relative effectiveness in recovery of active chymosin from various precursor renaturation procedures.

TABLE I

Chymosin Recovery After Various Precursor Renaturation Schemes

| Treatment | Disruption Method | |
|---|---|---|
| | Sonication | Enzyme |
| Insoluble fraction from cell lysate | 7% | — |
| Buffer washed insoluble fraction | 1% | 36% |
| Insoluble fraction after extraction with Triton X-100 | 100% | 31% |
| Insoluble fraction after extraction with Tween-20 | 1% | — |

As seen in Table I only low levels of active product (less than 10% of maximal) can be recovered if the Triton X-100 extraction is omitted. The substitution of another non-ionic detergent Tween-20 ™, did not facilitate the recovery of high levels of active product; however, it was efficient as a means for extracting the insoluble proteins from bacterial membranes and proteineous debris. Reducing the viscosity of the initial cell lysate by enzymatic digestion of the bacterial DNA with pancreatic DNase results in low yields of activity from the chymosin precursor protein after its activation and these product yields are not improved by a Triton X-100 extraction step. Thus, the combination of physical disruption of the bacterial lysate (by sonication) followed by extraction with Triton X-100 is a novel and unexpected requirement for the present invention relating to activation of chymosin.

The second essential feature of this process is the combined use of urea and alkaline pH buffer to solubilize and renature the chymosin precursor protein. Complete solubilization of the insoluble chymosin precursor protein can occur in 8M urea or alkali alone. However, the use of each of these reagents alone have several disadvantages. Solubilization with urea is very rapid but renaturation from urea requires a dialysis step which is very slow. Solubilization with alkali is slower than with urea and is complicated by an irreversible inactivation of the protein which begins after 20 minutes of incubation at pH 11.0 which is approximately the time required for complete solubilization of the chymosin precursor protein. Rapid renaturation from alkaline pH can be achieved by acidification. By simply combining these two procedures we observed a significant improvement in chymosin activity recovered in the final product (see FIG. 2). The rapid solubilization in urea is combined with dilution in an alkaline pH buffer and rapid renaturation occurs by a pH neutralization.

The successful renaturation of purified calf prochymosin is dependent on prochymosin concentration during the renaturation reaction. Likewise, a more efficient recovery of active chymosin from the insoluble chymosin precursor isolated from E. coli is dependent on the extent of dilution of the urea solubilized material into the alkaline pH buffer (see FIG. 4). The maximal level of chymosin activity achieved by the present invention is greater than or equal to 80% of the predicted limit based upon our estimates of chymosin precursor protein levels in the E. coli lysate and the known specific activity of calf stomach chymosin.

1. Isolation of mRNA

Preparation of Tissue: Rennin is synthesized by the gastric glands located in the mucosal tissue of the fourth stomach (abomasum) of unweaned calves. This tissue was obtained from a local abattoir. The stomachs were removed from freshly slaughtered animals and packed in ice. The abomasum, which is the most prominent stomach in the unweaned calf, was inspected for the presence of "cheese" (to insure the animal was pre-ruminant) and washed with water. The mucosal material was scraped from the stomach and quickly frozen in a dry ice-methanol bath. An average of 80 grams of tissue was obtained from each animal. Since mRNA degrades rapidly, the tissues were frozen immediately after sacrifice of the animal and stored at −70° C. until needed.

Isolation of RNA: The mucosal tissue contains high levels of mRNA to direct the synthesis of rennin. Total cellular RNA was extracted from the mucosal tissue, and then the mRNA population was specifically isolated. In order to protect cellular RNA from degradation, the tissue was weighed and then quickly submerged in a solution of guanidinium thiocyanate to inhibit cellular RNAse as described by Ullrich, A. et al., Science 196. 1313-1319 (1977). The tissue was thoroughly macerated in a Waring blender, and the RNA was isolated by sedimentation through a CsCl cushion by the procedure of V. Glisin, R. Crkvenjakov, and C. Byus, Biochem. 13, 2633-2637 (1974). The total weight of mucosal tissue used as starting material was 13.3 grams. From this, 8.5 milligrams of total cellular RNA was recovered. This yield (0.06%) is within the expected range of 0.01-1%.

Purification of mRNA: The mRNA fraction of total cellular RNA differs from other RNA species in that it contains 15-40 adenylic acid residues on the 3'-end of the molecule. The mRNA population was purified by chromatography on oligo-dT cellulose as described by Aviz, J. and Leder, P., Proc. Natl. Acad. USA 69, 1408-1412 (1972). The mRNA molecules anneal to the column by virtue of the polyadenylated tail and can be selectively purified. From the 8.5 milligrams of calf stomach RNA purified by the above procedure 30.8 micrograms of mRNA was recovered. The mRNA population comprises approximately 2% of the total RNA. Our yield of 0.35% is less than 2% and indicates that the non-messenger RNA species have been removed. The mRNA population contains RNA templates for all proteins which were actively synthesized by the unweaned calf abomasum at the time of death. Rennin should comprise 1%-5% of the total protein in the abomasum. Thus, if the mRNA is 50% pure, 0.5%-2.5% of the final clones should contain rennin sequences.

2. Translation of Rennin mRNA in Vitro

Before this mRNA was used as a template for the in vitro DNA synthesis it was essential to verify that molecules coding for preprorennin were present. A cell free extract of rabbit reticulocytes (reticulocyte lysate) will faithfully translate purified mRNA into protein in vitro (Pelham, H.R.B. and Jackson, R.J. Eur. J. Biochem. 67, 247-256, 1976). In this system the abomasum-derived mRNA directed the synthesis of at least twelve distinct polypeptide species which ranged in molecular weight from 17,000 to 102,000 daltons. The bands were discrete and few short peptides were synthesized. The most prominent species had an apparent molecular weight of 38,000-41,000, the approximate size of preprorennin. This is also the size of prepepsinogen, another enzyme synthesized by the abomasum tissue. To confirm that the mRNA purified from the abomasum did direct the synthesis of preprorennin, the in vitro translation products were precipitated with anti-serum raised in rabbits against purified calf rennin. Only one major band was precipitated by the anti-serum, and the molecular weight was between 38,000-41,000, which is consistent with preprorennin. Similar translation assays with prorennin mRNA were also carried out in frog oocytes with the same result.

3. Identification of Rennin-Specific mRNA Species

In addition to in vitro translation to identify rennin mRNA within the mRNA population from calf abomasum, hybridization of the mRNA with rennin-specific probes was also carried out. The sequence of the rennin-specific probes was derived from the amino acid sequence published by Foltmann, B., et al., J. Biol. Chem. 254, 8447-8456 (1979). From the universal genetic code, the probable DNA sequence of a gene or template can be predicted from the amino acid sequence of the protein. The DNA sequence is only probable because the code is degenerate13 some amino acids are represented by more than one codon. An analysis of the amino acid sequence of prorennin pointed to two regions containing only amino acids with unique codons. Fortunately, these regions are not sequences common between prorennin and pepsinogen. In these two small regions the genetic code predicts exactly the mRNA sequence. Oligomers complementary to these short sequences of genetic information were synthesized for use as probes. The smaller probe of 12 nucleotides (GTTCAT-CATGTT) is complementary to the genetic information for amino acids 183-186 of rennin. The second probe contains a mixture of two 14-mers (TACTGCTGTTTCTG and TACTGCTGGTTCTG) and is analogous to amino acids 29-33.

Hybridization to rennin-specific RNA was carried out using the procedures of Shinnick, T.M. et al., Nucl. Acids Res. 2, 1911-29 (1975). The abomasum mRNA was size-fractionated on an agarose gel which was then dried. The synthetic oligomers were radioactively labeled with $32_p$ to serve as probes for complementary mRNA sequences. The dried gel was incubated with the radioactive probes and subsequently washed. The radioactive probe will remain bound to the gel by hybridization to complementary sequences in the mRNA. Therefore, hybridization to an RNA band within the agarose gel suggests that rennin-specific mRNA was present in a particular size class. These regions of complementarity could be visualized following autoradiography. A full length preprorennin mRNA would have to be at least 1095 nucleotides in length to contain the codon for all 365 amino acids of the prorennin polypeptide. Both probes hybridized to the same region of the gel representing mRNA of 1350 bases. When mRNA recovered from this region of a parallel gel was translated in vitro, using the rabbit reticulocyte lysate system, it directed the synthesis of polypeptides of molecular weights 38-41,000. Hence, these data provide strong evidence that mRNA population contained molecules that specifically encode for preprorennin.

4. Synthesis of cDNA

The rennin of mRNA preparation was transcribed into cDNA for cloning in bacteria by the action of reverse transcriptase as described by Ullrich, A., et al. supra. Transcription was initiated at the 3'-polyadenylated tail of rennin mRNA using oligo-dT as a primer. Specifically, ten micrograms of oligo-dT was annealed to ten micrograms of purified mRNA in the presence of 50 mM NaCl. The annealing reaction was heated to 90.C and then slowly cooled. For the reverse transcriptase reaction, deoxynucleosidetriphosphates (A,T,G,C) were added to 0.5 mM along with 40 units of enzyme. The reverse transcriptase reaction buffer was as follows: 15 mM Tris-HCl, pH 8.3, 21 mM KCl, 8 mM $MgCl_2$, 0.1 mM EDTA, and 30 mM 2-mercaptoethanol. This mixture was incubated at 42.C for 45 minutes. The RNA-DNA duplex was disrupted by boiling for three minutes.

The second DNA strand was copied using DNA polymerase (The Klenow fragment). Following transcription of the first DNA strand by reverse transcriptase, a hairpin loop is generated at the end of the DNA transcript that can be used to prime the second DNA strand. The reverse transcriptase reaction mixture was diluted 1:1 with Klenow buffer (35 mM KCl, mM Tris-HCl, pH 8.3, 4 mM MgCl2, and 15 mM 2-mercaptoethanol) and 15 units of purified Klenow fragment was added. The enzyme mixture was incubated at 14.C for 3 hours and then at 4.C for 16 hours. The duplex DNA was precipitated with ethanol at this point. The nuclease $S_1$ buffer (25 mM sodium acetate, pH 4.5, 300 mM NaCl, and 1 mM $ZnCl_2$) and 1000 units of $S_1$ was added. The S1 reaction was incubated for 90 minutes at 37° C. Following this reaction, the DNA was again precipitated with ethanol.

Transcription of mRNA into the first strand of cDNA using reverse transcriptase is very inefficient, and premature termination if frequent. In order to enrich for full length copies cDNA and eliminate the screening of many clones containing short cDNA molecules, the cDNA preparation was subjected to polyacrylamide gel electrophoresis. The region of the gel corresponding to molecular sizes of 1.0 to 1.5 kb of DNA was excised, and the DNA removed by electroelution. From the original ten micrograms of purified mRNA, 300 nanograms of electrophoretically purified cDNA was recovered.

5. Construction of the Rennin cDNA Plasmid

For isolation of rennin-specific DNA, the blunt-ended cDNA molecules were inserted into bacterial plasmids. We utilized the GC tailing method of Chang, A.C.Y. Nature 275, 617-624 (1978) to insert the cDNA molecules into the plasmid pBR322 (Bolivar, F. et al., Gene 2, 95-113, 1977). Polycytidylic acid residues were polymerized onto the ends of the cDNA molecules using the enzyme terminal deoxynucleotidyl transferase, and polyguanidylic acid residues were added to the ends of the linear form of pBR322. The two tailed DNA preparations were annealed to generate recombinate DNA molecules.

In the formation of cDNA plasmids, ten nanograms of purified cDNA was used. The cDNA was added to the terminal transferase reaction containing: 140 mM potassium cacodylate, 25 mM Tris, pH 7.6, 1 mM $CoCl_2$, and 0.2 mM DTT. Since polycytidylic acid residues were polymerized onto the cDNA molecules, dCTP was added to 1.5 mM. This mixture was prewarmed to 37° C. and then 15 units terminal transferase was added. The enzyme reaction was stopped after four minutes by the addition of EDTA to 5 mM.

The reaction was extracted with phenol, and the DNA was precipitated with ethanol. The plasmid DNA pBR322 was digested with the restriction enzyme Pst I, and then polyguanidylic acid residues were polymerized onto ends of the linear molecule as described above.

At this point, the tailed cDNA molecules were recombined with bacterial plasmid DNA by annealing of the complementary ends. The two preparations of dC-tailed cDNA and dG-tailed pBR322 DNA were mixed in annealing buffer (0.1 M NaCl, 10 mM Tris, pH 7.5, and 0.25 mM EDTA) and heated to 80 C. The mixture was allowed to slow cool to 37° C. and then to 26° C.

The recombinant DNA molecules were then introduced into bacteria by transformation. The *Escherichia coli* strain K-12 MM 294 (ATCC Accession No. 31446) was used. Other host cells could also be used for this step. The transformed bacteria were inoculated onto agar plates containing the antibiotic tetracycline. Since the plasmid pBR322 contains the tetracycline resistance gene, only those bacteria which have acquired a recombinant plasmid will survive. These bacteria will each grow and divide to form a bacterial colony. Each cell in the colony will be a descendant of the original parental cell and will contain the same recombinant plasmid. From the ten nanograms of cDNA used to make recombinant plasmids, 2000 clones were obtained and further screened for rennin sequences.

6. Identification of Rennin Clones

The isolated colonies containing recombinant plasmid DNA were screened using the procedures of Grunstein, M., and Hogness, D.S., Proc. Natl. Acad. Sci. USA 72 3961-3965 (1975). Each recombinant clone was inoculated into a numbered well of a microtiter plate and also onto nitrocellulose filters where the bacteria can grow as isolated colonies. The colonies on the filter were lysed, and filter was then washed to remove cell membranes and proteins The bacterial DNA, including chromosomal and the recombinant plasmid, specifically adhere to the nitrocellulose filter.

The analysis of the genetic content of plasmid DNA depends on the availability of an appropriate probe. Previously it was demonstrated that the 12-mer and 14-mer were specific probes for rennin in that they hybridized to only a single region of the RNA gels corresponding to prorennin mRNA. These probes were therefore used to identify recombinant plasmids which might contain prorennin sequences. (Wallace, R.B. et al, Nucl. Acids Res. 9, 879–894, 1981). The nitrocellulose filters which had been inoculated with bacterial clones containing recombinant plasmids were immersed in a solution of either the radioactively labeled 12-mer or 14-mer. The labeled oligonucleotides will bind to the filter only when they hybridize to complementary sequences in the recombinant DNA. Areas of radioactivity on the filter are identified by autoradiography. In this manner, from the 2000 clones whose recombinant plasmids were screened, 18 were positive by hybridization to the radioactive probes. This result of 0.9% was within the expected range of 0.5-2.5% positive clones predicted from our estimate of the percentage of rennin mRNA in the cells of the abomasum.

7. Analysis of Clones that Hybridize to Rennin-Specific Clones

The cultures corresponding to the positive plasmids were grown for further analysis. Plasmid DNA was purified from all positive rennin clones, and the size of the inserted cDNA determined by digestion with Pst I, followed by gel electrophoresis. Only two clones contained cDNA inserts large enough to contain all of the genetic information for a full length copy of rennin. This was not an unexpected result, since the initial transcription step in the synthesis of cDNA from mRNA is prone to premature termination. The two clones selected for further study were 5G3 which contained an insert of over 1.4 kb and 15C5 with an insert of 1.2 kb.

The recombinant plasmids were digested with a variety of restriction endonucleases to determine the position of key restriction sites within the cDNA clones. From this restriction analysis, the two restriction maps presented in FIG. 1 were generated. The position of key restriction sites within the cloned material is needed to develop a strategy to sequence the rennin DNA. This sequence analysis was necessary to verify that our clones contain sequences for authentic rennin.

The clones, 5G3 and 15C5, were sequenced by the method of Maxam, A. and Gilbert, W. Proc. Nat. Acad. USA 74, 560–564 (1977). Fragments were generated initially by restriction enzyme digestion of the DNA with either Pst I, Bam HI or Taq I. Other enzymes were also used when necessary. The fragments were labelled with $^{32}P$ either by the enzyme T4 polynucleotide kinase or by DNA polymerase I (Klenow fragment) (Maxam and Gilbert, supra).

Both clones were sequenced in their entirety using this method. In addition, 80% of 5G3 and 70% of 15C5 were sequenced on both strands. The homology between the two clones is 100% in the overlapping areas (FIG. 1). Only the clone 5G3 is full length and contains all the sequences encoding preprorennin. In addition, 5G3 contains an additional 250 bases on the 5'-end of the rennin structural gene. This region is derived from an inverted repeat of the carboxy region of rennin along with sequences from the untranslated region between the termination codon and the poly A addition site. The clone 15C5 begins at amino acid 6 of prorennin and includes approximately 100 additional nucleotides from the untranslated region on the 3'-end of the structural gene. Both clones encode sequences for the A form of rennin.

Comparison of 5G3 and 15C5 with the published sequences of Harris et al., supra, indicated very few differences. The sequence varied at the codons for amino acid 258 and 320, but these were singled base differences which did not alter the amino acid. The sequence from Harris et al., supra, also showed a difference a the codon for amino acid 286 that does alter the amino acid to the B form of rennin. The sequence published by Moir et al., supra, is the A form similar to 5G3 and 15C5 and shows no sequence difference. The complete preprorennin sequences of Harris et al., supra, and Moir et al., supra, were derived from sequence data of several overlapping clones. Neither group obtained a full length copy of the preprorennin clone.

Our predicted amino acid sequence (FIG. 6) agrees with the sequence of the A form of rennin published by Foltmann et al., supra except for the presence of an asparagine codon at amino acid 202 that replaces the aspartic acid. This difference may or may not be significant since a common problem in protein sequence analysis is the difficulty in differentiating between asparagine and aspartic acid.

8. Construction of Polypeptide Expression Plasmid

Cloned cDNA from eukaryotic sources usually does not contain the proper signals to effect proper transcription and translation in *E. coli*. Following isolation of appropriate cDNA clones, the eukaryotic DNA must be manipulated so that it can be recognized by the protein synthetic machinery of the host procaryotic cell. In order to synthesize prorennin-derived polypeptide in *E. coli*, a recombinant plasmid was constructed that directs the synthesis of a fusion protein comprising some amino acids derived from a normal bacterial protein, B-galactosidase, and prorennin polypeptide. Our construction utilized the promotor, ribosome binding site and the several amino acids from the N-terminus of B-galactosidase including the initiator methionine. These sequences were joined in phase via common restriction endonuclease sites with rennin-derived sequences. In the bacterial cell, prorennin-derived polypeptide will be synthesized as a fusion protein but during acid activation of the polypeptide, the bacterial amino acids are cleaved off and the mature polypeptide recovered.

The B-galactosidase sequences used in this construction were derived from the plasmid pUC8 (J. Messing, R. Crea, and P.H. Seeburg. Nucl. Acids Res. 9, 309-321, 1981). In this plasmid, a synthetic oligonucleotide containing convenient restriction endonuclease cleavage sites was inserted near the sequences coding for the N-terminal amino acids of beta-galactosidase. The prorennin-derived sequences were inserted in the synthetic region downstream from the initiator codon and in phase with this codon.

In the first step of this construction, a 70 bp fragment was removed from the cDNA clone 5G3 by digestion with the enzymes Bam HI and Pst I. This 70 bp fragment contained the coding sequences for amino acids 6 through 28 of the prorennin-derived polypeptide. The plasmid pUC8 was also digested with Bam HI and Pst I, and then ligated with the 70 bp fragment via cohesive termini to generate the recombinant plasmid, pLCl (FIG. 7a). After this ligation step, the prorennin-derived sequences were not in phase with coding sequences of B-galactosidase. In order to change the reading frame, pLCl was digested with Bam HI to linearize the plasmid, and the overhanging ends were filled-in with the Klenow fragment of DNA polymerase. After ligation, a Cla I restriction site was generated at the site of the former Bam HI site (FIG. 7b).

This plasmid (pLC2) was digested with Pst I, followed by treatment with bacterial alkaline phosphatase. The rennin-derived cDNA clone 5G3 was also digested with Pst I, and the 1 kb fragment containing sequences coding for amino acids 29 to the carboxy-terminus of the prorennin-derived polypeptide was isolated. The 1 kb Pst I fragment from 5G3 was ligated into the Pst I linearized plasmid pLC2, and clones were screened for the proper orientation of the 1 kb Pst I fragment. One clone (pLC7) contained the prorennin-derived sequence fused in phase with B-galactosidase (FIGS. 7c, 8). The pLC7 prorennin expression plasmid includes sequences which code for both the pseudorennin and mature rennin cleavable sites between amino acids 28-29 and amino acids 42-43, respectively. This clone was used for polypeptide expression and activity assays.

9. Expression and Analysis of Cloned Gene Products

Proteins encoded by the pLC7 DNA were synthesized and identified in three systems: first, by coupled in vitro transcription/translation; second, by radio-labeling minicell gene products; and third, by fractionation of whole E. coli cells. The polypeptides produced in these three systems were electrophoresed on polyacrylamide gels to compare the molecular weights of the plasmid-encoded products with those of authentic prorennin and rennin.

The in vitro transcription/translation system uses the bacterial components necessary for the transcription and translation of plasmid encoded genes in a cell-free environment as described by Zubay, G. Ann. Rev. Gen. 7, 267-287 (1973), and modified by Andrews, W. and Rawson, J. Plasmid 8, 148 (1982). When cloned pLC7 DNA was introduced into this system, radio-labeled protein which co-electrophorese with calf prorennin (M.W. of 41,000) could be detected.

Under acidic conditions, calf prorennin undergoes cleavage to smaller molecular weight forms that demonstrate milk-clotting activity. Efficient acid activation requires the concentration of prorennin to be greater than 5 ug/ml. Therefore, the addition of unlabeled calf prorennin (at a final concentration of 0.1 mg/ml) to the in vitro mixture containing pLC7 polypeptide product was necessary to visualize acid activation. Upon acid activation of a mixture of radiolabeled LC7 polypeptide and calf prorennin, both demonstrated a change in mobility corresponding to conversion of prorennin to pseudorennin (M.W. of 38,000) when activated at pH 2 or to rennin (M.W. of 36,000) when activated at pH 4.5. Thus, the pLC7 encoded polypeptide can be cleaved at the appropriate pH to smaller molecular weight polypeptides which are the same size as pseudorennin and rennin.

The synthesis of pLC7-encoded polypeptide was also analyzed in minicells. Minicells are products of aberrant cell division of strains that carry the min A and min B mutations. The minicells bud off from the parental cell and contain the E. coli transcription/ translation system but lack chromosomal DNA. Minicells can be easily fractionated from parental whole cells. When a minicell-producing strain is transformed with plasmid DNA, the minicells will contain plasmid DNA and synthesize plasmid-encoded proteins. Isolated minicells from the minicell producing strain P678-54 transformed with cloned pLC7 DNA produces specific polypeptide which co-electrophoreses with calf prorennin (M.W. =41,000) and the LC7 polypeptide produced in the in vitro system. When the minicell preparation containing the pLC7-encoded product was fractionated into soluble and membrane compartments, the 41,000 molecular weight radio-labeled polypeptide co-purified with the membrane components.

Whole E. coli cells were also transformed with pLC7 plasmid DNA. The transformed cells were then separated into cytoplasmic, inner membrane and outer membrane fractions Diedrich, D.L., Summers, A.O., and Schnaitman, C.A., J. Bact. 131, 598-607 (1977) as modified by MacGregor, C.H., Bishop, C.W., and Blech, J.E., J. Bact. 137, 574-583 (1979). The pLC7 plasmid encodes a 41,000 M.W. (prorennin size) polypeptide which co-purifies with the outer membrane compartment of the cell. It was not possible to demonstrate acid dependent cleavage of the pLC7 polypeptide while it was associated with the insoluble membrane fraction of the cell.

10. Extraction of Prorennin-Derived Polypeptide from Insoluble State

From the analyses of fractionated whole cells and minicells, it appeared that the pLC7 polypeptide must be purified away from the insoluble membrane components in order to demonstrate milk-clotting activity. In order to extract pLC7 polypeptide activity, cell membranes were treated with a non-ionic detergent to remove contaminating protein components, and the remaining nonsolubilized material, which contained the LC7 polypeptide, was then solubilized in a protein denaturing agent which unfolds most proteins to a random coil structure. The purpose of this treatment is to extract the LC7 polypeptide from E. Coli material and to unfold the polypeptide. Production of native LC7 polypeptide requires refolding of the extracted and denatured polypeptide by the removal of the denaturing agent. The pLC7 polypeptide can be further purified by chromatography before or after the denaturing agents are removed from the protein solution.

EXAMPLE 1

The E. coli strain JM83 (Bethesda Research Laboratories, Inc.) was transformed with pLC7 and grown in L-broth media supplemented with antibiotic. Five grams of JM83/pLC7 cell paste was suspended in buffer containing lysozyme, sonicated, and the mixture was centrifuged. The membrane pellet was suspended in a weight excess of Triton X-100 detergent, and the insoluble material (containing LC7 polypeptide) was collected by centrifugation. This pellet was then solubilized in 6-8M urea. The urea was removed by dialysis in a large volume of buffer lacking urea. This extracted LC7 polypeptide can be acid activated and displays milk-clotting activity (Section 11).

EXAMPLE 2

The membrane fraction was isolated and extracted with 6-8M urea as described in Example 1. This protein solution was then contacted with an ionic chromatographic resin (DEAE-cellulose) and the urea was removed by washing the protein-resin complex. The protein was then eluted from the resin with a salt solution. The soluble protein thus collected contained the LC7 polypeptide which can be acid-activated and will clot milk (Section 11).

EXAMPLE 3

The membrane fraction containing LC7 polypeptide was solubilized in urea and contacted with DEAE-cellulose as in Example 2. LC7 polypeptide was purified by elution of the protein with a gradient of NaCl (0-1M) containing 5-8M urea. Fractions containing the LC7 polypeptide in urea were pooled and the urea was then removed by dialysis. The extracted and purified LC7 polypeptide can be acid activated and contains milk-clotting activity (Section 11).

Following extraction of the LC7 polypeptide in the denaturing agent, several purification procedures were attempted. The presence of LC7 polypeptide was demonstrated by appropriate size of the protein after electrophoresis on polyacrylamide gels (Section 9) and/or milk-clotting activity (Section 11).

EXAMPLE 4

The membrane fraction of JM83/pLC7 was isolated and extracted with 5-8M urea as described in Example 1. The urea was removed by dialysis. The solution containing LC7 polypeptide was then contacted with an ionic chromatographic resin (DEAE cellulose). The LC7 polypeptide was eluted from the resin with a gradient solution of NaCl (0-1M). The LC7 polypeptide was resolved into two fractions: one containing LC7 polypeptide in a form that can be acid activated and can clot milk and one containing inactive LC7 polypeptide.

EXAMPLE 5

A solution containing urea extracted and dialysed LC7 polypeptide (see Example 1) was contacted with a hydrophobic chromatographic material; e.g. phenyl-Sepharose (Pharmacia). This material appears to act as an affinity ligand resin. After elution of the protein-resin complex with a gradient solution containing decreasing salt and increasing non-ionic detergent concentrations, LC7 polypeptide is resolved into separate fractions containing respectively, polypeptide that could not be activated and polypeptide which could be acid activated.

Purification initiated after the removal of the denaturing agent can resolve the LC7 polypeptide into two forms: one which is capable of milk-clotting after activation and one which cannot be activated in this state. LC7 polypeptide which remains inactive can be treated to repeated renaturation steps as described in Example 4 and then repurified. Such recycling of LC7 polypeptide allows maximal recovery of active material.

EXAMPLE 6

A preparation of membrane material containing LC7 polypeptide was extracted with 5-8 M urea and dialyzed. This solution was then contacted with an ionic chromatographic resin (Example 4) and resolved into two fractions: one which could be acid-activated and one which remained inactive after acidification. The solution containing the inactive form of LC7 polypeptide was again exposed to 5-8 M urea dialyzed and contacted with the same ionic chromatographic resin. Upon elution from the resin with a salt gradient, native LC7 polypeptide was recovered in significant yields.

11. Activation and Assay of
    Prorennin-Derived Polypeptide

The presence of active LC7 polypeptide was demonstrated by its ability to clot milk following acid or proteolytic treatment. The milk clot assay is as described by B. Foltmann, Methods in Enzymology, 19, 421-436 (1970). The assay solution is composed of 50 mg per ml of nonfat milk powder in water plus 50 mM CaCl, with the pH adjusted to 6.0. The reaction is carried out at 30° C. One unit of activity is defined as the amount of enzyme which will clot 1 ml of milk substrate in 100 seconds at 30° C.

Activation of extracted LC7 polypeptide can occur by treatment of this protein with acid or by proteolytic digestion of the LC7 polypeptide with other enzymes. This activation process is then terminated by addition of various chemical agents. The resultant product of the activation of LC7 polypeptide material can be detected by analysis on polyacrylamide gels or by the clotting of a milk solution in the conventional way.

EXAMPLE 7

A solution of LC7 polypeptide which had been urea extracted and then dialyzed was acidified to (pH 2 or pH 4.5) with hydrochloric acid for a time sufficient for maximal activation as measured by the increase in milk-clotting activity. The activity of the solution was unaffected by neutralization to pH 5-7 with a basic solution.

EXAMPLE 8

A solution of LC7 polypeptide prepared as in Example 1 was treated with trypsin, a proteolytic enzyme, in a buffered solution. The interaction of these two materials continues until maximal activation was achieved, as measured by the increase in milk-clotting activity. The trypsin was then chemically inactivated or physically separated from the activated LC7 polypeptide.

The LC7 prorennin polypeptide is produced in JM83 cells in amounts which constitute at least 1.0% of the total protein of the bacterium, in the range of 10,000 -20,000 molecules per cell. The level of expression is ten-fold greater than previously published attempts to clone and express a milk-clotting enzyme from rennin mRNA (Alford, B.L. et al., supra). Samples of acid-activated LC7 polypeptide prepared from $E.$ $coli$ have a specific activity greater than 500 units/mg of purified protein. This is greater than 20% of the specific activity of purified calf enzyme.

The LC7 polypeptide was acid activated at pH 2 to a pseudo-rennin size material and its activity compared to pseudo-rennin derived from purified calf prorennin. By the criteria described above these two enzymatic activities were indistinguishable. These two enzymes also produce similar digestion products upon their addition to a solution of milk or purified caseins.

The recombinant DNA and its host microorganism described herein as JM83/pLC7 was deposited on Mar. 25, 1983 with the American Type Culture Collection, Rockville, Md. and assigned ATCC Accession No. 39325.

EXAMPLE 9

A second plasmid, pWHA49, was constructed which contains a eukaryotic structural gene coding for pro-chymosin. This plasmid was used to transform $E.$ $coli$ using techniques as previously described. 10g of frozen cell paste of E. coli strain CY15001 containing pWHA49 were suspended in 100 mls of 25 mm Tris-HCl pH 8, 10 mm EDTA, 1 mg/ml lysozyme. After a short incubation, the lysed cells were further disrupted by sonication. Partial purification of the pWHA49 encoded pro-chymosin protein was effected by centrifugation at 10,000×g for ten minutes, followed by an overnight detergent extraction of the pelleted cell debris with 8 percent final concentration of Triton X-100 detergent (Sigma Chemical Co.). The pWHA49 prochymosin protein remained in the insoluble, particulate pellet after the procedure.

Authentic calf prochymosin is a soluble enzyme which can be rapidly activated by acid treatment to a form which efficiently coagulates milk. The E. coli synthesized pWHA49 prochymosin, isolated as described, was insoluble and showed no enzymatic activity after acid treatment.

The pWHA49 prochymosin pellet was suspended in 6.3 mls of 10 mM sodium phosphate buffer at pH 7.5. The suspension is fully solubilized by the addition of solid urea to a final concentration of 6-8 M and then mixed for 16 hours at room temperature.

The resultant clear solution was diluted into 100 volumes (1000 mls) of 25 mM sodium phosphate buffer at pH 11.0, mixed thoroughly and allowed to stand for 10 minutes at room temperature. The pH of the solution was then titrated to pH 8.3 by addition of 0.2N HCl over a period of 3 minutes.

The resultant solution was left at room temperature for one hour or more, after which time acidification to a pH greater than 1.5 and less than 5.0 generated a chymosin milk-clotting activity. Acid activation of native calf prochymosin and of pWHA49 prochymosin resulted in the same size proteins, that is, treatment at pH 2 produced pseudochymosin having a molecular weight of approximately 38,500 and treatment at pH 4.5 produced chymosin at a molecular weight of 36,000 (see FIG. 3). The renatured, activated product has 50-95 percent of the specific activity of natural calf chymosin and has the same limited substrate specificity (see FIG. 4).

The process utilizing urea and alkali demonstrated improvements in renaturing prochymosin, when compared to methods using a single reagent (see FIG. 2).

Although the foregoing invention has been described in some detail by way of illustration and example for purposes of clarity of understanding, it will be obvious to one skilled in the art that certain changes and modifications may be practiced within the scope of the appended claims.

What is claimed is:

1. A process for isolating a heterologous polypeptide produced as an inclusion body in transforming bacteria wherein the improvement
    a) lysing said transformed bacteria containing said polypeptide to form a lysate;
    b) contacting said lysate with a solution containing a weight excess of a non-ionic detergent sufficient to maintain said polypeptide in an insoluble state and solubilizing the cellular debris; and,
    c) separating the insoluble polypeptide from the soluble debris.

2. The process of claim 1, wherein said bacteria are *Escherichia coli*.

3. The process of claim 1, wherein said nonionic detergent comprises Triton X-100.

4. The process of claim 1 wherein the lysate is centrifuged prior to step (b) to form a pellet containing the insoluble protein.

5. The process of claim 1, wherein said polypeptide is prochymosin.

* * * * *

UNITED STATES PATENT AND TRADEMARK OFFICE
CERTIFICATE OF CORRECTION

PATENT NO. : 5,082,775

DATED : January 21, 1992

INVENTOR(S) : McCaman, et al.

It is certified that error appears in the above-identified patent and that said Letters Patent is hereby corrected as shown below:

In column 1, line 20, delete "E. coli" and substitute therefor, --E. coli,--;

In column 4, line 16, delete "nonionic" and substitute therefor, --non-ionic--;

In column 6, line 50, delete "pH" and substitute therefor, --pH 2.0--;

In column 9, line 22, delete "E. coli" and substitute therefor, --*E. coli*--;

In column 9, line 54, delete "196." and substitute therefor, --196,--;

In column 10, line 53, delete "13" and substitute therefor, -- -- --;

In column 11, line 50, delete "KCI" and substitute therefor, --KCl--;

In column 11, line 51, delete "HCI" and substitute therefor, --HCl--;

In column 11, line 51, delete "MgCl2" and substitute therefor, --$MgCl_2$--;

In column 13, line 8, delete "Wallace, R.B. et al," and substitute therefor, --Wallace, R.B. et al.,--;

UNITED STATES PATENT AND TRADEMARK OFFICE
CERTIFICATE OF CORRECTION

PATENT NO. : 5,082,775

DATED : January 21, 1992

INVENTOR(S) : McCaman, et al.

It is certified that error appears in the above-identified patent and that said Letters Patent is hereby corrected as shown below:

In column 14, line 63, delete "pLC1" and substitute therefor, --pLC1 --;

In column 14, line 67, delete "pLCI" and substitute therefor, --pLC1--;

In column 19, line 8, delete "E. coli" and substitute therefor, --E. coli--;

In column 20, line 15, delete "improvement" and substitute therefor, --improvement is:--;

In column 20, line 26, delete "nonionic" and substitute therefor, --non-ionic--.

Signed and Sealed this

Nineteenth Day of October, 1993

Attest:

BRUCE LEHMAN

*Attesting Officer*   *Commissioner of Patents and Trademarks*